US00PP24420P3

(12) United States Plant Patent
Zaiger et al.

(10) Patent No.: US PP24,420 P3
(45) Date of Patent: May 6, 2014

(54) PEACH TREE NAMED 'SNOW PRIDE'

(50) Latin Name: *Prunus persica*
Varietal Denomination: Snow Pride

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 202 days.

(21) Appl. No.: 13/506,122

(22) Filed: Mar. 29, 2012

(65) Prior Publication Data

US 2013/0263340 P1 Oct. 3, 2013

(51) Int. Cl.
*A01H 5/00* (2006.01)

(52) U.S. Cl.
USPC ..... Plt./195

(58) Field of Classification Search
USPC ..... Plt./195
See application file for complete search history.

*Primary Examiner* — June Hwu
*Assistant Examiner* — Louanne Krawczewicz Myers

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features: the tree being a regular and productive bearer of large size fruit; the tree with vigorous, upright growth; producing fruit with an attractive red skin color; fruit with very good flavor and eating quality with a low to sub acid, mild, sweet flavor; and fruit with good storage and shipping quality.

1 Drawing Sheet

Botanical designation: *Prunus persica.*
Variety denomination: 'Snow Pride'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

2. Prior Varieties

Among the existing varieties of peach trees, which are known to us, and mentioned herein, 'September Snow' Peach (U.S. Plant Pat. No. 8,003) and the proprietary peach seedling selections '237LP27', '370LU525', '55GF90', '66EG140', '32LG569' and '58EG528', all of which are non-patented.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from seed of a first generation cross between our two proprietary non-patented peach seedling selections '237LP27' and '370LU525'. The seed parent '237LP27' (non-patented) originated from crosses between the following selections; 'September Snow' Peach (U.S. Plant Pat. No. 8,003) and the proprietary seedling selections '55GF90' peach (non-patented) and '66EG140' peach (non-patented). The pollen parent '370LU525' (non-patented) originated from crosses between the following varieties; 'Sweet September' Peach (U.S. Plant Pat. No. 9,964) and the proprietary seedling selections '32LG569' peach (non-patented), '58EG528' peach (non-patented) and '66EG140' peach (non-patented). A large number of these first generation seedlings were grown on their own root system. Under close and careful observation, one such seedling, which is the present variety, exhibited desirable tree and fruit characteristics and was selected in 2007 for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a productive and regular bearer of large size, clingstone fruit with low to subacid, mild, sweet flesh that has very good flavor and eating quality. The fruit is further characterized by having an attractive red skin color, firm white flesh and being relatively uniform in size. In comparison to the proprietary seed parent '237LP27' (non-patented) the fruit of the new variety is larger in size and is approximately 6 days earlier in maturity. In comparison to the proprietary pollen parent '370LU525' (non-patented) the fruit of the new variety has firmer flesh, more attractive red skin color and is approximately 15 days later in maturity. In comparison to the commercial variety 'September Snow' Peach (U.S. Plant Pat. No. 8,003) the fruit of the new variety is approximately 16 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color.

Tree:

*Size.*—Large, usually pruned to 3 to 3.5 meters in height and width for economical harvesting of fruit. Size varies with different cultural practices.

*Vigor.*—Vigorous, growth of 1.5 to 2 meters in height the first growing season. Varies with fertility of soil, climatic conditions and cultural practices.

*Form.*—Upright, usually pruned to vase shape.

*Branching habit.*—Upright, crotch angle approximately 35°, increases with heavy crop load.

*Productivity.*—Productive, fruit thinning and spacing necessary for desired market size. Fruit set varies with climatic conditions during blooming season.

*Bearer.*—Regular, adequate fruit set 3 consecutive years. No alternate bearing observed.

*Fertility.*—Self fertile.

*Density.*—Medium dense, usually pruned to vase shape to allow more sunlight to center of tree to enhance fruit color and health of fruit wood.

*Hardiness.*—Hardy in all stone fruit growing areas of California. Tree grown in USDA Hardiness Zone 9. Winter chilling requirement approximately 850 hours at or below 45° F.

Trunk:

*Size.*—Medium. Average circumference 45.7 cm at 30.5 cm above ground on a 5 year old tree.

*Stocky.*—Medium stocky.

*Texture.*—Medium shaggy, roughness increases with age.

*Color.*—Varies from 2.5Y 6/2 to 5Y 5/2.

Branches:

*Size.*—Medium. Average circumference 16.3 cm at 1.0 meter above ground. Crotch angle approximately 35°, increases with heavy crop load.

*Surface texture.*—New growth relatively smooth. Mature growth medium rough, roughness increases with age of growth.

*Lenticels.*—Average number 22 in a 25.8 sq cm area. Average length 5.3 mm. Average width 2.0 mm. Color varies from 10YR 5/10 to 7.5YR 5/8.

*Color.*—New growth varies from 5GY 7/6 to 5GY 6/6 with 2.5YR 3/8 where exposed to sunlight. Mature growth varies from 10YR 3/4 to 10YR 3/6, varies with age of growth.

Leaves:

*Size.*—Medium. Average length 140.8 mm. Average width 39.4 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slightly indented over midrib and leaf veins, glabrous. Lower surface relatively smooth except for small ridges created by midrib and pinnate venation, glabrous.

*Petiole.*—Average length 11.8 mm. Average width 1.1 mm. Longitudinally grooved. Color varies from 5GY 5/6 to 5GY 5/8. Surface glabrous.

*Stipules.*—Average length 3.8 mm. Average number 2. Margin — pectinate. Color varies from 5GY 5/6 to 5GY 5/8.

*Glands.*—Type — reniform. Size — small. Average length 1.0 mm. Average diameter 0.4 mm. Average number 2, varies from 1 to 4. Located primarily on base of leaf blade and upper portion of petiole. Color varies from 5GY 5/6 with 10R 2/4.

*Color.*—Upper surface varies from 10GY 3/2 to 10GY 2/4. Lower surface varies from 2.5GY 3/4 to 10GY 3/4. Midvein color varies from 2.5GY 7/2 to 10Y 7/2.

Flower buds:

*Size.*—Medium to large. Average length 16.7 mm. Average diameter 9.3 mm.

*Hardiness.*—Hardy with respect to California winters.

*Form.*—Plump, conical, becoming elongated before opening.

*Pedicel.*—Average length 5.2 mm. Average width 1.2 mm. Color varies from 5GY 6/6 to 5GY 6/8.

*Color.*—Varies from 7.5RP 6/12 to 5RP 7/8.

Flowers:

*Blooming period.*—Date of First Bloom Mar. 4, 2011. Date of Petal Fall Mar. 13, 2011, varies slightly with climatic conditions.

*Size.*—Large, showy. Average height 21.4 mm. Average diameter 42.6 mm.

*Petals.*—Normally 5, alternately arranged to sepals. Size — large. Average length 21.6 mm. Average width 17.9 mm. Form — orbicular. Margin — sinuate. Both upper and lower surfaces glabrous. Color varies from 5RP 7/6 to 5RP 7/8, fades with age of flower.

*Sepals.*—Normally 5, alternately arranged to petals. Size — large. Average length 5.6 mm. Average width 4.5 mm. Shape — triangular, apex rounded. Margin — entire. Upper surface — glabrous. Lower surface — pubescent. Color — upper surface varies from 5GY 5/6 to 5R 3/6. Lower surface varies from 2.5R 3/4 to 5R 2/4.

*Stamens.*—Average number per flower — 36. Average filament length 16.6 mm. Filament color varies from N 9.5/(white) to 5RP 5/10. Anther color varies from 7.5R 4/12 to 7.5R 3/10.

*Pollen.*—Self fertile. Color varies from 5Y 7/10 to 5Y 7/12.

*Pistil.*—Normally one. Surface — pubescent. Average length 19.6 mm. Position of stigma is even with anthers. Color varies from 2.5GY 8/6 to 2.5GY 7/6.

*Fragrance.*—Moderate aroma.

*Color.*—Varies from 5RP 7/6 to 5RP 8/4.

*Number flowers per flower bud.*—One.

*Pedicel.*—Average length 5.6 mm. Average width 1.4 mm. Color varies from 2.5GY 6/8 to 5GY 5/6.

Fruit:

*Maturity when described.*—Firm ripe.

*Date of first picking.*—Sep. 5, 2011.

*Date of last picking.*—Sep. 12, 2011, varies slightly with climatic conditions.

*Size.*—Large. Average diameter axially 74.3 mm. Average transversely in suture plane 81.6 mm. Average weight 284.0 grams, varies slightly with fertility of the soil, amount of thinning and climatic conditions.

*Form.*—Globose.

*Suture.*—Nearly smooth, extends from base to apex.

*Ventral surface.*—Nearly smooth, very slightly lipped.

*Apex.*—Varies from slightly retuse to very small tip.

*Base.*—Rounded.

*Stem cavity.*—Rounded to slightly elongated in suture plane. Average depth 8.7 mm. Average diameter 9.4 mm.

Stem:

*Size.*—Small to medium. Average length 9.7 mm. Average diameter 3.0 mm.

*Color.*—Varies from 10Y 7/6 to 10Y 6/6.

Flesh:

*Ripens.*—Evenly.

*Texture.*—Firm, meaty, crisp.

*Fibers.*—Few, small, tender.

*Firmness.*—Good, comparable to the commercial peach variety 'September Snow' (U.S. Plant Pat. No. 8,003).

*Aroma.*—Slight.

*Amydgalin.*—Undetected.

*Eating quality.*—Very good.

*Flavor.*—Very good, low to subacid, mild and sweet.

*Juice.*—Moderate amount, enhances flavor.

*Brix.*—Average Brix 11.1°, varies slightly with amount of fruit per tree and climatic conditions.

*Color.*—Varies from 10Y 9/2 to 2.5GY 9/2 with 5R 4/10 to 5R 4/8 around pit.

*Pit cavity.*—Average length 34.4 mm. Average width 25.3 mm. Average depth 10.4 mm. Color varies from 5R 3/8 to 7.5R 3/8.

Skin:

*Thickness.*—Medium.

*Surface.*—Smooth.

*Pubescence.*—Moderate amount, short in length.

*Tendency to crack.*—None.

*Color.*—Ground color light yellow, varies from 2.5Y 8/4 to 5Y 8/4. Overspread with 5R 3/4 to 7.5R 2/6.

*Tenacity.*—Tenacious to flesh.

*Astringency.*—Undetected.

Stone:

*Type.*—Clingstone.

*Size.*—Large. Average length 33.4 mm. Average width 24.3 mm. Average thickness 18.8 mm.

*Form.*—Obovoid.

*Base.*—Flat.

*Apex.*—Varies from round to slightly pointed. Average length 0.5 mm.

*Surface.*—Pitted throughout, pits vary from round to elongated.

*Sides.*—Unequal, with one side extending further from suture plane.

*Ridges.*—Numerous small ridges extending from base to apex.

*Tendency to split.*—None.

*Color.*—Varies from 5R 2/4 to 7.5R 2/4 when dry.

Kernel:

*Size.*—Large. Average length 18.5 mm. Average width 11.5 mm. Average depth 6.6 mm.

*Form.*—Ovoid.

*Viability.*—Viable, complete embryo development.

*Skin.*—Color varies from 5R 2/6 to 7.5R 2/4.

Use: Dessert.

*Market.*—Local and long distance.

Keeping quality: Good, held firm in cold storage at 38° to 42° F. for 3 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

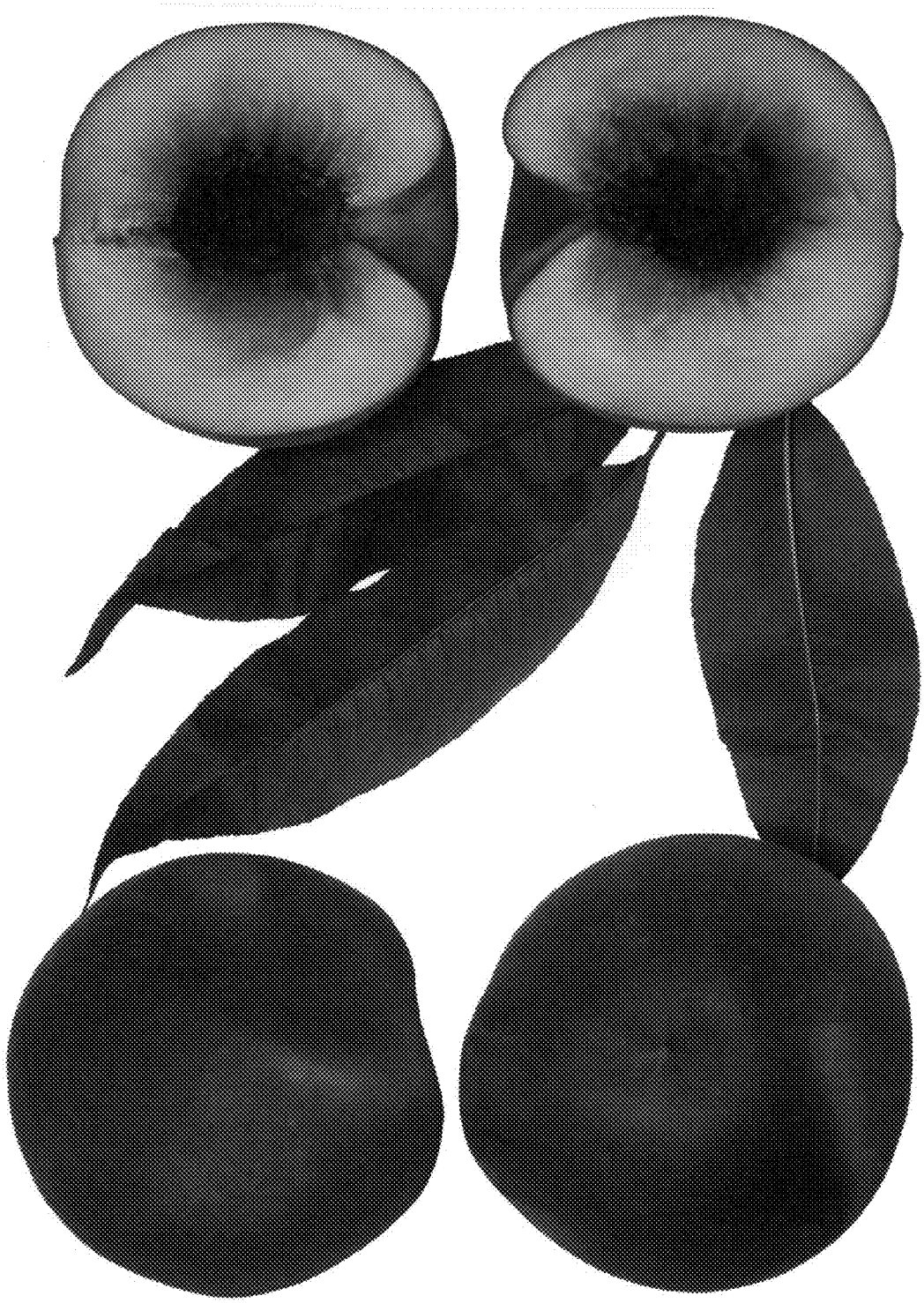

* * * * *